(12) United States Patent
Sato

(10) Patent No.: US 9,402,978 B2
(45) Date of Patent: Aug. 2, 2016

(54) GUIDEWIRE

(71) Applicant: TERUMO KABUSHIKI KAISHA, Shibuya-ku (JP)

(72) Inventor: Hideo Sato, Fujinomiya (JP)

(73) Assignee: Terumo Kabushiki Kaisha, Shibuya-ku, Tokyo (JP)

( * ) Notice: Subject to any disclaimer, the term of this patent is extended or adjusted under 35 U.S.C. 154(b) by 0 days.

(21) Appl. No.: 14/483,793

(22) Filed: Sep. 11, 2014

(65) Prior Publication Data

US 2015/0005746 A1 Jan. 1, 2015

Related U.S. Application Data

(63) Continuation of application No. PCT/JP2012/078950, filed on Nov. 8, 2012.

(30) Foreign Application Priority Data

Mar. 16, 2012 (JP) .................................. 2012-060597

(51) Int. Cl.
*A61B 5/00* (2006.01)
*A61M 25/09* (2006.01)

(52) U.S. Cl.
CPC ..... *A61M 25/09* (2013.01); *A61M 2025/09083* (2013.01); *A61M 2025/09091* (2013.01); *A61M 2025/09133* (2013.01)

(58) Field of Classification Search
CPC .................. A61M 25/09; A61M 2025/09083; A61M 2025/09091; A61M 2025/09133
USPC ....................................................... 600/585
See application file for complete search history.

(56) References Cited

U.S. PATENT DOCUMENTS 7,618,379 B2 * 11/2009 Reynolds .............. A61L 31/022
600/433
8,206,837 B2 * 6/2012 Mishima ............... A61M 25/09
428/586

(Continued)

FOREIGN PATENT DOCUMENTS

EP 0 820 782 A2 1/1998
EP 2 263 735 A1 12/2010

(Continued)

OTHER PUBLICATIONS

International Search Report (PCT/ISA/210) mailed on Jan. 22, 2013, by the Japanese Patent Office as the International Searching Authority for International Application No. PCT/JP2012/078950.

(Continued)

*Primary Examiner* — Max Hindenburg
(74) *Attorney, Agent, or Firm* — Buchanan, Ingersoll & Rooney PC

(57) ABSTRACT

A guidewire includes a wire body having a first wire arranged on a distal end side and a second wire arranged on a proximal end side of the first wire. A proximal end surface of the first wire and a distal end surface of the second wire are joined to each other to form a joint portion. An outer member is arranged on an outer peripheral side of the wire body and forms a tubular shape which covers the wire body at least from a distal end portion of the first wire to the joint portion. An inner member is arranged between an outer peripheral portion of the wire body and an inner peripheral portion of the outer member and covers the joint portion. The inner member is an inner coil formed by winding a wire for the inner member into a coil shape.

19 Claims, 10 Drawing Sheets

(56) References Cited

U.S. PATENT DOCUMENTS

| | | | |
|---|---|---|---|
| 8,500,657 B2 * | 8/2013 | Brown | A61M 25/09 600/585 |
| 8,585,612 B2 * | 11/2013 | Nishigishi | A61M 25/09 600/585 |
| 8,622,932 B2 * | 1/2014 | Matsumoto | A61M 25/09 600/585 |
| 2008/0183182 A1 | 7/2008 | Satou et al. | |
| 2008/0262474 A1 | 10/2008 | Northrop | |
| 2010/0318001 A1 | 12/2010 | Miyata et al. | |

FOREIGN PATENT DOCUMENTS

| | | |
|---|---|---|
| EP | 2 338 555 A2 | 6/2011 |
| JP | 2008-161589 A | 7/2008 |
| JP | 2011-000199 A | 1/2011 |
| WO | 2008/034010 A2 | 3/2008 |

OTHER PUBLICATIONS

Extended European search report issued Oct. 22, 2015 in the corresponding European Patent Application No. 12871031.6. (9 pages).

* cited by examiner

GUIDEWIRE

CROSS REFERENCES TO RELATED APPLICATIONS

This application is a continuation of International Application No. PCT/JP2012/078950 filed on Nov. 8, 2012 and claims priority to Japanese Application No. 2012-060597 filed on Mar. 16, 2012, the entire content of both of which is incorporated herein by reference.

TECHNICAL FIELD

The present invention relates to a guidewire.

BACKGROUND DISCUSSION

A guidewire is used to guide a catheter in a medical treatment to a site having a surgical difficulty, or a medical treatment aiming to minimize injury to a human body, such as percutaneous transluminal coronary angioplasty (PTCA), for example, and a medical examination such as cardiovascular radiography. The guidewire used for PTCA is inserted into the vicinity of an angiostenosis portion, which is the target site, together with a balloon catheter in a state where a distal end of the guidewire is protruded from a distal end of the balloon catheter. The guidewire guides a distal end portion of the balloon catheter to the vicinity of the angiostenosis portion.

In percutaneous transluminal angioplasty (PTA), which is substantially similar to PTCA, the distal end portion of the balloon catheter is guided to the vicinity of the angiostenosis portion by using the guidewire to open a stenosis portion (closed portion) formed in a peripheral blood vessel such as femoral, iliac, renal, and shunt blood vessels.

The blood vessels to which these medical treatment methods are applied are intricately curved. Therefore, the guidewire used when the balloon catheter is inserted into the blood vessel requires flexibility and resilience for moderate bending, pushing performance and torque transmission performance (these are generically referred to as "operability") for transmitting an operation in a proximal end portion to a distal end thereof, and also kink resistance (bending resistance).

Known guidewires have a first wire made of a Ni—Ti-based alloy and a second wire made of stainless steel (for example, refer to JP-A-2008-161589). In the guidewire disclosed in JP-A-2008-161589, a guidewire is provided in which a proximal end surface of the first wire and a proximal end surface of the second wire are joined to each other to form a joint portion, and the joint portion is covered with a coil from an outer peripheral side thereof. When this guidewire is used, there is a possibility that the following situations may occur depending on the magnitude of an operator's operating force.

For example, the first wire and the second wire have considerably different rigidity. Consequently, there is a possibility that the wires in the joint portion are unintentionally bent or, on the other hand, the joint portion is caused to have a rigidity much stronger than that of the leading and trailing portions thereof, and thus the joint portion is unlikely to be curved along the curves of the blood vessel.

In addition, in the guidewire disclosed in JP-A-2008-161589, a guidewire is also disclosed in which a proximal end portion of the first wire and a proximal end portion of the second wire are connected to each other via a pipe. When this guidewire is used, depending on the magnitude of the operator's operating force, there is a possibility that the rigidity of a portion between the first wire and the second wire becomes very strong in the pipe, and thus the guidewire is unlikely to be curved.

SUMMARY

The disclosure here provides a guidewire having excellent operability.

More particularly, an exemplary embodiment of the disclosure provides a guidewire including a wire body that has a first wire which is arranged on a distal end side and a second wire which is arranged on a proximal end side of the first wire and is formed of a material whose rigidity is higher than that of a material of the first wire, and in which a proximal end surface of the first wire and a distal end surface of the second wire are joined to each other so as to form a joint portion. An outer member is arranged on an outer peripheral side of the wire body and forms a tubular shape which covers the wire body at least from a distal end portion of the first wire to the joint portion, and has flexibility. An inner member is arranged between an outer peripheral portion of the wire body and an inner peripheral portion of the outer member, and covers the joint portion. The inner member is an inner coil formed by winding a wire for the inner member into a coil shape.

In addition, in the guidewire of an exemplary embodiment of the disclosure, it is preferable that the inner coil has a distal end portion and a proximal end portion, and at least any one of these is stretchable.

In addition, it is preferable that the joint portion has an outer diameter which is the same as an outer diameter of a proximal end of the first wire on a distal end side and an outer diameter of a distal end of the second wire on a proximal end side, respectively, and that an inner diameter of the inner coil is larger than an outer diameter of the joint portion.

Further, in the guidewire of an exemplary embodiment of the disclosure, it is preferable that a horizontal cross-sectional shape of the wire for the inner member has a circular shape or a flat shape.

Still further, it is preferable that the outer member is configured to have a first outer coil which is located on a distal end side and is formed by winding a wire for a first outer member into a coil shape and a second outer coil which is connected to a proximal end side of the first outer coil and is formed by winding a wire for a second outer member into a coil shape, and that the wire for the inner member is the thinnest wire among the wire for the first outer member, the wire for the second outer member, and the wire for the inner member.

A guidewire according to a further exemplary embodiment of the disclosure includes a wire body that has a first wire which is arranged on a distal end side and a second wire which is arranged on a proximal end side of the first wire and is formed of a material whose rigidity is higher than that of a material of the first wire, and in which a proximal end surface of the first wire and a distal end surface of the second wire are joined to each other so as to form a joint portion. An outer member is arranged on an outer peripheral side of the wire body and forms a tubular shape which covers the wire body at least from a distal end portion of the first wire to the joint portion, and has flexibility. An inner member is arranged between an outer peripheral portion of the wire body and an inner peripheral portion of the outer member, and covers the joint portion. The inner member has a tubular shape and has multiple penetrating holes which penetrate a tube wall thereof.

In addition, it is preferable that the respective penetrating holes are respectively formed along a circumferential direction of the inner member.

Further, in the guidewire according to an exemplary embodiment of the disclosure, it is preferable that the inner member has a function of relieving stress generated in the joint portion in a state where the guidewire is used.

It is also preferable that the first outer coil has a gap between the adjacent wires for the first outer member, that in the second outer coil, the adjacent wires for the second outer member are in contact with each other, and that in the inner coil, the adjacent wires for the inner member are apart from each other.

Still further, it is preferable that winding directions of the wire for the first outer member, the wire for the second outer member, and the wire for the inner member are the same as one another.

In addition, in the guidewire according to an exemplary embodiment of the disclosure, it is preferable that the winding directions of the wire for the first outer member and the wire for the second outer member are the same as each other, and the winding direction of the wire for the inner member is opposite to the winding directions of the wire for the first outer member and the wire for the second outer member.

Further, it is preferable that the inner peripheral portion of the inner member is apart from the outer peripheral portion of the wire body.

Still further, it is preferable that the outer peripheral portion of the inner member is apart from the inner peripheral portion of the outer member.

Also, in the guidewire according to an exemplary embodiment of the disclosure, it is preferable that in the inner member, at least any one between the distal end portion and the proximal end portion thereof is supported with respect to the wire body.

In addition, it is preferable that the guidewire includes a fixing member which fixes a longitudinally intermediate portion of the outer member to the first wire.

Further, it is preferable that the fixing member also fixes the inner member to the wire body.

In addition, in the guidewire according to an exemplary embodiment of the disclosure, it is preferable that the inner member is extended so that the distal end portion thereof protrudes from the fixing member in a direction toward the distal end.

Further, it is preferable that the outer member is configured to have the first outer coil which is located on the distal end side and has a coil shape, and the second outer coil which is connected to the proximal end side of the first outer coil and has a coil shape.

Still further, it is preferable that the inner member is more flexible than the first outer coil.

Also, it is preferable that a material of the first outer coil and a material of the second outer coil are different from each other.

In addition, it is preferable that a material of the first outer coil and a material of the inner member are the same as each other.

In addition, in the guidewire according to an exemplary embodiment of the disclosure, it is preferable that the proximal end portion of the first wire has a first wire side constant outer diameter portion whose outer diameter is constant, that the distal end portion of the second wire has a second wire side constant outer diameter portion whose outer diameter is constant, and that the outer diameter of the first wire side constant outer diameter portion and the outer diameter of the second wire side constant outer diameter portion are the same as each other.

In addition, it is preferable that the first wire has a first wire side tapered portion whose outer diameter gradually decreases in a direction toward the distal end, on the distal end side of the first wire side constant outer diameter portion.

Further, it is preferable that the second wire has a second wire side tapered portion whose outer diameter gradually increases in a direction toward the proximal end, on the proximal end side of the second wire side constant outer diameter portion.

When a guidewire is being used, a torque acting around an axis thereof, a pushing force acting from a proximal end side thereof, and a pressing force acting from a curved blood vessel (force which bends the guidewire) are applied to the guidewire. In this case, stress is generated in a joined portion formed by a first wire and a second wire being joined to each other. However, according to an exemplary embodiment of the disclosure, the stress is reliably relieved by an inner member. This can reliably prevent a problem in which the guidewire is unintentionally bent in the joint portion or is broken in the joint portion, while the guidewire is used (operated). Accordingly, the guidewire exhibits excellent torque transmission performance, pushing performance, and kink resistance, for example.

In addition, according to the disclosure herein, the inner member allows smooth transition of rigidity from the second wire to the first wire. This enables the guidewire to be smoothly curved even near the joint portion when the guidewire is inserted into the curved blood vessel, thereby improving an ability to follow the blood vessel. That is, the operability of the guidewire is improved.

DETAILED DESCRIPTION

Hereinafter, a guidewire according to the disclosure herein will be described in detail with reference to preferred exemplary embodiments illustrated in the accompanying drawings.

Figure 1:
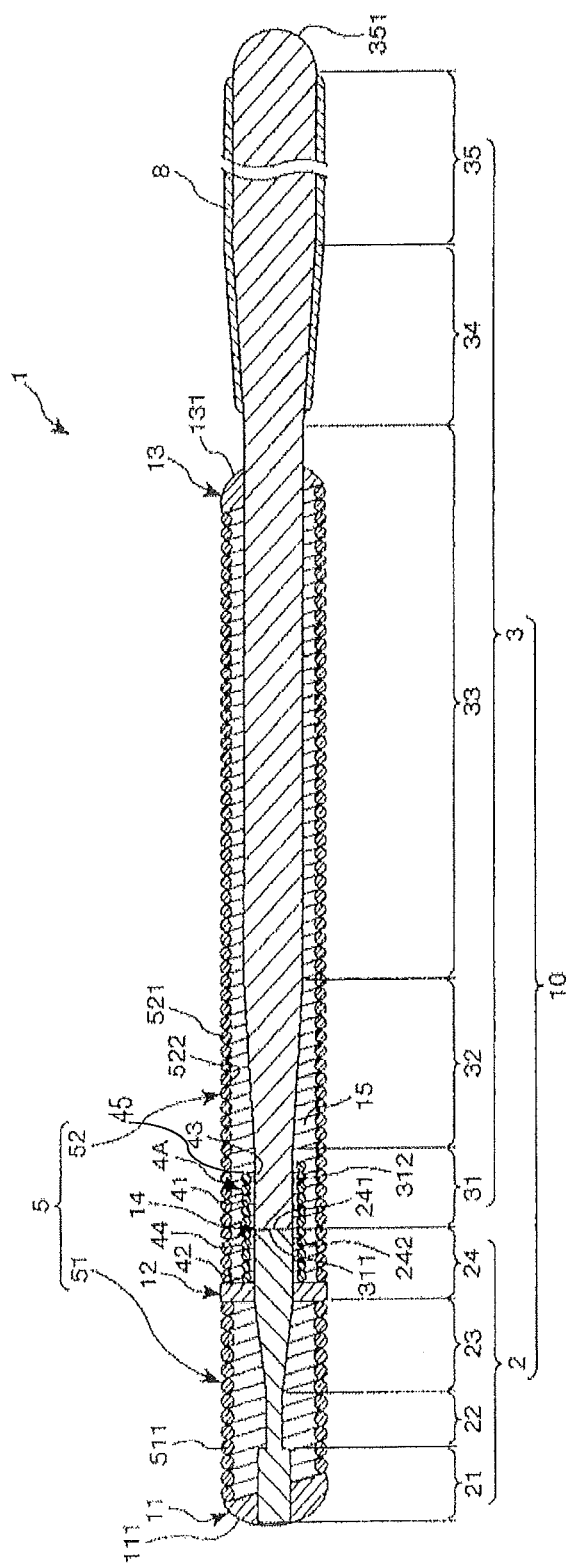
FIG. 1 is a longitudinal cross-sectional view illustrating a first exemplary embodiment of a guidewire according to the disclosure.

FIG. 1 is a longitudinal cross-sectional view illustrating a first exemplary embodiment of a guidewire according to the disclosure herein. For convenience of description, the right side in FIG. 1 (FIGS. 2 to 10 are also the same) is referred to as a "proximal end", the left side is referred to as a "distal end". In addition, in FIG. 1 (FIGS. 2 to 10 are also the same), in order to facilitate understanding, the guidewire is schematically illustrated by shortening a longitudinal direction of the guidewire and by exaggeratingly widening a thickness direction of the guidewire. Accordingly, the illustrated ratio between the longitudinal direction and the thickness direction is different from an actual ratio.

A guidewire 1 illustrated in FIG. 1 is a guidewire used to guide a catheter (balloon catheter) in a medical treatment to a site having a surgical difficulty, such as percutaneous transluminal coronary angioplasty (PTCA), for example. In PTCA, the guidewire 1 is inserted into the vicinity of an angiostenosis portion, which is the target site, together with the catheter in a state where a distal end of the guidewire 1 is protruded from a distal end of the catheter. The guidewire 1 guides a distal end portion of the catheter to the vicinity of the angiostenosis portion. Note that, although not particularly limited, it is preferable that the overall length of the guidewire 1 is 200 mm to 5,000 mm.

The guidewire 1 includes a wire body 10, an outer member 5 which is arranged on an outer peripheral side of the wire body 10, and an inner member 4A which is arranged between an outer peripheral portion of the wire body 10 and an inner peripheral portion of the outer member 5. Hereinafter, a configuration of each portion will be described in greater detail.

The wire body 10 has a first wire 2 which is arranged on a distal end side and a second wire 3 which is arranged adjacent to a proximal end side of the first wire 2, and is formed by joining (connecting) the first wire 2 and the second wire 3 to each other.

The first wire 2 is composed of a wire rod having flexibility and/or elasticity. A preferable material for the wire rod (first wire 2) includes a Ni—Ti-based alloy such as Ni—Ti alloys of Ni of 49 atomic % to 52 atomic %, for example. The Ni—Ti-based alloy is relatively flexible, has resilience, and is unlikely to have a bending tendency. Therefore, if the first wire 2 is formed of the Ni—Ti-based alloy, in the guidewire 1, a portion on the distal end side can obtain sufficient flexibility and resilience against bending. An ability to follow the complicated curved and bent blood vessel is improved and excellent operability can be obtained. Even when the first wire 2 is deformed by being repeatedly curved and bent, the resilience provided for the first wire 2 does not increase the bending tendency thereof. Accordingly, while the guidewire 1 is used, it is possible to prevent the operability from being degraded due to the bending tendency occurring in the first wire 2.

The Ni—Ti alloy having the above-described composition may also have super-elasticity through heat treatment or the like. However, even those which contain Ni of more than 52 atomic % and do not substantially show super-elasticity can be used, as long as they have moderate flexibility and elasticity.

The first wire 2 is configured so that a flat plate portion 21, a first constant outer diameter portion 22, a tapered portion (first wire side tapered portion) 23, and a second constant outer diameter portion (first wire side constant outer diameter portion) 24 are formed sequentially from the distal end side.

The flat plate portion 21 is a portion which has a plate shape (i.e., planar or ribbon shape), and in which a thickness and a width are constant in the longitudinal direction of the wire. This flat plate portion 21 can be used by being deformed (reshaped: newly shaped) into a desired shape. In general, a doctor sometimes uses the guidewire 1 by deforming the distal end portion of the guidewire into a desired shape in advance, so that the distal end portion of the guiding catheter or the like corresponds to a shape of the blood vessel, or so that the distal end portion is smoothly guided by properly selecting a course at a diverging point of the blood vessel. Bending the distal end portion of the guidewire 1 into a desired shape as described above is called reshaping. Providing the flat plate portion 21 on the guidewire 1 facilitates the reshaping and enables the reshaping to be reliably performed, thereby significantly improving the operability when the guidewire 1 is inserted into the blood vessel.

The first constant outer diameter portion 22 is a portion whose outer diameter is constant along the longitudinal direction of the wire. It is preferable that the outer diameter of the first constant outer diameter portion 22 is larger than the thickness of the flat plate portion 21 and is smaller than the width of the flat plate portion 21.

The tapered portion 23 is a portion whose outer diameter gradually decreases in a direction toward the distal end. Since the first wire 2 has the tapered portion 23, it is possible to gradually decrease the rigidity (flexural rigidity and torsional rigidity) of the first wire 2 in the direction toward the distal end. As a result, the guidewire 1 obtains excellent flexibility in the distal end portion thereof, thereby improving the ability to follow the blood vessel or the like and safety. Furthermore, it is possible to prevent bending. Note that, the outer diameter of the distal end of the tapered portion 23 is preferably the same as the outer diameter of the first constant outer diameter portion 22. In addition, a taper angle (decreasing rate of the outer diameter) of the tapered portion 23 may be constant along the longitudinal direction of the wire, or the tapered portion 23 may have a portion which varies along the longitudinal direction of the wire. For example, a portion having a relatively large taper angle (decreasing rate of the outer diameter) and a portion having a relatively small taper angle may be alternately and repeatedly formed multiple times.

The second constant outer diameter portion 24 is a portion whose outer diameter is constant in the longitudinal direction of the wire. The outer diameter of the second constant outer diameter portion 24 is substantially the same as the outer diameter of the proximal end of the tapered portion 23.

The distal end (distal end surface 311) of the second wire 3 is connected to the proximal end (proximal end surface 241) of the first wire 2 by welding, for example. The second wire 3 has a flexibility and elasticity similar to the first wire 2, and is composed of a wire rod having a rigidity which is higher than that of the material (Ni—Ti-based alloy) of the first wire 2. A suitable material of this wire rod (second wire 3) is not particularly limited, but includes various metallic materials such as stainless steel and a cobalt-based alloy, for example.

For example, the stainless steel includes all SUS product types such as SUS304, SUS303, SUS316, SUS316L, SUS316J1, SUS316J1L, SUS405, SUS430, SUS434, SUS444, SUS429, SUS430F, SUS302, and the like.

In addition, any cobalt-based alloy may be used as long as the cobalt-based alloy contains Co as a constituting element. However, it is preferable to use a cobalt-based alloy which contains Co as a main component (Co-based alloy: alloy in which a content of Co is highest in a weight ratio within all elements constituting the alloy). It is more preferable to use a Co—Ni—Cr-based alloy. The cobalt-based alloy has a high elastic modulus when used in the wire, and has a moderate elastic limit. Therefore, the second wire 3 formed of the cobalt-based alloy has excellent torque transmission performance, and is very unlikely to suffer from a problem of buckling. In addition, the cobalt-based alloy has a high elastic modulus, and is cold-formable even with a high elastic limit. Since the cobalt-based alloy has a high elastic limit, it is possible to sufficiently prevent the occurrence of buckling, to decrease the diameter, and to provide the wire with sufficient flexibility and rigidity so as to be inserted into a predetermined site.

As the Co—Ni—Cr-based alloy, for example, it is preferable to use an alloy having a composition of Co of 28 wt % to 50 wt %-Ni of 10 wt % to 30 wt %-Cr of 10 wt % to 30 wt %-Fe for the remaining portion, or an alloy in which a portion thereof is substituted by other elements (substituting element). Allowing the alloy to contain the substituting elements demonstrates an inherent advantageous effect depending on the substituted element. For example, it is possible to obtain further improved strength of the second wire 3 by containing at least one type selected from Ti, Nb, Ta, Be, and Mo as the substituting element. Note that, in a case of containing elements other than Co, Ni, and Cr, it is preferable that the content thereof (of the whole substituting elements) is 30 wt % or less.

In addition, a portion of Co, Ni, and Cr may be substituted by other elements. For example, a portion of Ni may be substituted by Mn. Accordingly, this can achieve further improved workability, for example. In addition, a portion of Cr may be substituted by Mo and/or W. This can achieve a further improved elastic limit. Out of the Co—Ni—Cr-based alloys, it is particularly preferable to use a Co—Ni—Cr—Mo-based alloy which contains Mo.

The second wire 3 is configured so that a first constant outer diameter portion (second wire side constant outer diameter portion) 31, a first tapered portion (second wire side tapered portion) 32, a second constant outer diameter portion 33, a second tapered portion 34, and a third constant outer diameter portion 35 are formed sequentially from the distal end side.

The first constant outer diameter portion 31 is a portion whose outer diameter is constant along the longitudinal direction of the wire. The outer diameter of the first constant outer diameter portion 31 is substantially the same as the outer diameter of the second constant outer diameter portion of the first wire 2.

The first tapered portion 32 is a portion whose outer diameter gradually increases in a direction toward the proximal end.

The second constant outer diameter portion 33 is a portion whose outer diameter is constant along the longitudinal direction of the wire.

The second tapered portion 34 is a portion whose outer diameter gradually increases in a direction toward the proximal end.

In combination, the first constant outer diameter portion 31, the first tapered portion 32, the second constant outer diameter portion 33, and the second tapered portion 34 allow physical characteristics of the guidewire 1, particularly the elasticity, to be smoothly changed from the second wire 3 to the first wire 2.

The third constant outer diameter portion 35 is a portion whose outer diameter is constant along the longitudinal direction of the wire. The third constant outer diameter portion 35 functions as a grip portion which is gripped by a user to operate the guidewire 1. It is preferable that a proximal end surface 351 of the third constant outer diameter portion 35 has a round shape.

In the exemplary embodiment, a resin coating layer 8 which covers an outer peripheral surface of the second wire 3 is preferably disposed on the second wire 3 from the second tapered portion 34 to the third constant outer diameter portion 35. This resin coating layer 8 may be formed for various purposes, but as an example, it is useful for improving the operability for the guidewire 1 by reducing friction (sliding resistance) of the guidewire 1 and thereby improving sliding performance.

In order to reduce the friction (sliding resistance) of the guidewire 1, it is preferable that the resin coating layer 8 is formed of a material which can reduce the friction as described below. In this manner, frictional resistance (sliding resistance) between the guidewire 1 and the inner wall of the catheter used together with the guidewire 1 is reduced and the sliding performance is improved. Accordingly, the operability of the guidewire 1 inside the catheter increases. In addition, since the sliding resistance of the guidewire 1 is reduced, when the guidewire 1 is moved and/or rotated inside the catheter, it is possible to more reliably prevent kinks (bending) or torsion of the guidewire 1, particularly kinks or torsion near the joint portion 14.

For example, a material which can reduce this friction includes a polyolefin such as polyethylene and polypropylene, polyvinyl chloride, polyesters (PET, PBT, and the like), polyamides, polyimides, polyurethane, polystyrene, polycarbonate, silicone resins, and fluorine resins (PTFE, ETFE, and the like), or a composite material of these.

In addition, in some cases, the resin coating layer 8 may be provided for the purpose of improving safety when the guidewire 1 is inserted into the blood vessel. For this purpose, it is preferable that the resin coating layer 8 is formed of a material having sufficient flexibility (soft material, elastic material).

For example, a material having sufficient flexibility includes a polyolefin such as polyethylene and polypropylene, polyvinyl chloride, polyesters (PET, PBT, and the like), polyamides, polyimides, polyurethane, polystyrene, silicone resins, thermoplastic elastomers such as polyurethane elastomers, polyester elastomers, and polyamide elastomers, and various rubber materials such as latex rubber and silicone rubber, or a composite material in which two or more out of these are combined.

Note that, the resin coating layer 8 may have a single layer or may be a stacked body having two or more layers.

In addition, it is preferable that at least the distal end portion of the guidewire 1 is coated with a hydrophilic material. It is preferable that the guidewire 1 includes a layer formed of the hydrophilic material on an outer surface of the outer member 5 (to be described later). This causes the hydrophilic material to be wetted, thereby allowing lubrication performance such that the friction (sliding resistance) of the guidewire 1 is reduced, the sliding performance is improved, and the operability of the guidewire 1 is thereby improved.

By way of example, the hydrophilic material may include cellulose-based polymeric materials, polyethylene oxide-based polymeric materials, maleic anhydride-based polymeric substances (for example, maleic anhydride copolymers such as methyl vinyl ether-maleic anhydride copolymers), acrylamide-based polymeric materials (for example, block copolymers of polyacrylamide, polyglycidyl methacrylate-dimethyl acrylamide (PGMA-DMAA)), water-soluble nylon, polyvinyl alcohol, polyvinyl pyrrolidone, and the like.

In many cases, this hydrophilic material is wetted (absorbs water) to demonstrate the lubrication performance, and reduces the frictional resistance (sliding resistance) between the guidewire 1 and the inner wall of the catheter used together with the guidewire 1. This improves the sliding performance of the guidewire 1, thereby further improving the operability of the guidewire 1 inside the catheter.

In addition, in the guidewire 1, an average outer diameter of the first wire 2 is smaller than an average outer diameter of the second wire 3. This allows the guidewire 1 to have sufficient flexibility for the first wire 2 which forms the distal end side, and to have relatively high rigidity for the second wire 3 which forms the proximal end side. Therefore, it is possible to concurrently obtain flexibility of the distal end portion and excellent operability (pushing performance, torque transmission performance, and the like).

As described above, in the wire body 10, the proximal end surface 241 of the first wire 2 and the distal end surface 311 of the second wire 3 are joined to each other by welding. In this manner, in the wire body 10, the joint portion 14 is formed in an intermediate portion in the longitudinal direction of the wire.

The joint portion 14 can obtain relatively strong joint strength since the joint portion 14 is a portion formed by welding. A welding method for the first wire 2 and the second wire 3 is not particularly limited. For example, the welding method may include friction welding, spot welding using a laser, and butt resistance welding such as upset welding. However, it is particularly preferable to use butt resistance welding since the butt resistance welding is relatively simple and can obtain the high joint strength.

The joint portion 14 may be a portion which is joined by a brazing material. It is preferable that the proximal end surface 241 of the first wire 2 and the distal end surface 311 of the second wire 3 are joined to each other via the brazing material. It is preferable that the outer diameter including the brazing material portion is substantially the same as the second constant outer diameter portion 24 of the first wire 2 and the first constant outer diameter portion 31 of the second wire 3.

In addition, the joint portion 14 may be configured so that the proximal end surface 241 of the first wire 2 and the distal end surface 311 of the second wire 3 are joined to each other via an intermediate member. It is preferable that the intermediate member includes a distal end portion and a proximal end portion, and that the distal end portion of the intermediate member is welded to the proximal end surface 241 of the first wire 2, and the proximal end portion of the intermediate member is welded to the distal end surface 311 of the second wire 3. It is preferable that the outer diameter of the intermediate member is the same as the outer diameters of the second constant outer diameter portion 24 of the first wire 2 and the first constant outer diameter portion 31 of the second wire 3.

In addition, in the joint portion 14, the outer diameter thereof is the same as the outer diameter of the constant outer diameter portion 24 of the first wire 2 on the distal end side and the outer diameter of the constant outer diameter portion 31 of the second wire 3 on the proximal end side, respectively. This can sufficiently ensure the flexibility near the joint portion 14 or the resilience against bending, and at the same time, it is possible to maintain the strength of each wire and the joint portion 14.

In the wire body 10, a distal end side portion thereof is inserted into the outer member 5 having a tubular shape as a whole in a non-contact manner, in a natural state where an external force is not applied. In this manner, in the wire body 10, a section from the intermediate portion (distal end portion) of the flat plate portion 21 of the first wire 2, via the joint portion 14, to the intermediate portion of the second constant outer diameter portion 33 of the second wire 3 on the proximal end side which is located farther from the joint portion 14 is in a state of being covered with the outer member 5. The length of the outer member 5 is not limited as long as the outer member 5 covers at least a section from the distal end portion of the first wire 2 to the joint portion 14 of the wire body 10.

The outer member 5 has a tubular shape as a whole. In the exemplary configuration illustrated in FIG. 1, the outer member 5 is configured to have a first outer coil 51 which is located on the distal end side and a second outer coil 52 which is connected to the proximal end side of the first outer coil 51.

The first outer coil 51 is formed by winding a first wire (wire for the first outer member) 511 into a coil shape (spiral shape). In the first outer coil 51, the adjacent first wires 511 have a gap therebetween in a natural state where the external force is not applied, and accordingly are coarsely wound.

The second outer coil 52 is formed by winding a second wire (wire for the second outer member) 521 into a coil shape in a direction which is the same as that of the first outer coil 51. In the second outer coil 52, the adjacent second wires 521 are in contact with each other in the natural state, and accordingly are densely wound.

In addition, the overall length (length in the longitudinal direction of the wire) of the first outer coil 51 is shorter than the overall length (length in the longitudinal direction of the wire) of the second outer coil 52. This enables the first outer coil 51 to cover a section from the intermediate portion of the flat plate portion 21 of the first wire 2 to the vicinity of a boundary portion between the tapered portion 23 and the second constant outer diameter portion 24. In addition, the second outer coil 52 can cover a section from the vicinity of the boundary portion to the intermediate portion of the second constant outer diameter portion 33 of the second wire 3.

With the outer member 5 having the above-described configuration, the distal end side portion of the wire body 10 is covered with the outer member 5. Thus, it is possible to minimize an area in contact with the blood vessel wall. Accordingly, sliding resistance is reduced, and the operability of the guidewire 1 is further improved.

The inner diameter of the first outer coil 51 is preferably smaller than the inner diameter of the second outer coil 52.

The outer diameter of the first outer coil 51 and the outer diameter of the second outer coil 52 are each constant along the longitudinal direction of the wire, and are preferably the same as each other.

The diameter of the first wire 511 is larger than the diameter of the second wire 521.

The constituting material of the first wire 511 (first outer coil 51) may be the same as the constituting material of the second wire 521 (second outer coil 52). However, it is preferable that these materials are different from each other. When the constituting material of the first wire 511 and the constituting material of the second wire 521 are different from each other, it is preferable to use a radiopaque material as the configuring material of the first wire 511. For example, it is possible to use Pt or an alloy thereof (for example, Pt—Ni alloy, Pt—W alloy). As the constituting material of the second wire 521, it is preferable to use a material which is less radiopaque than the first wire 511. For example, similar to the constituting material of the second wire 3, it is possible to use stainless steel. It is preferable to use the above-described materials for the first wire 511, since it is possible to insert the guidewire 1 into a living body while checking a position of the distal end portion of the guidewire 1 by way of X-ray fluoroscopy.

As illustrated in FIG. 1, the outer member 5 is configured so that both end portions and the intermediate portion in the longitudinal direction are fixed to the wire body 10 respectively via the fixing materials (fixing members) 11, 12, and 13. This reliably prevents positional deviation of the outer member 5 in the longitudinal direction of the wire with respect to the wire body 10.

In the configuration illustrated in FIG. 1, in the first outer coil 51, the distal end portion thereof is fixed to the flat plate portion 21 of the wire body 10 via the fixing material 11, and the proximal end portion is fixed in the vicinity of the boundary portion between the tapered portion 23 of the wire body 10 and the second constant outer diameter portion 24 via the fixing material 12. In addition, in the second outer coil 52, the distal end portion thereof is fixed in the vicinity of the boundary portion between the tapered portion 23 of the wire body 10 and the second constant outer diameter portion 24, and the proximal end portion is fixed to the second constant outer diameter portion 33 of the wire body 10. The fixing material 12 has both functions of fixing the first outer coil 51 to the wire body 10 and fixing the second outer coil 52 to the wire body 10. Thus, the first outer coil 51 and the second outer coil 52 are connected to each other via the fixing material 12.

These fixing materials 11, 12, and 13 each are formed of solder (brazing material). The fixing materials 11, 12, and 13 may also be an adhesive, without being limited to the solder. In addition, in order to prevent damage to the inner wall of the body lumen such as the blood vessel, it is preferable that a distal end surface 111 of the fixing material 11 and a proximal end surface 131 of the fixing material 13 has a round shape.

As described above, in the wire body 10, the distal end side portion thereof is inserted into the outer member 5 in a non-contact manner. In this manner, a gap 15 is formed between the outer peripheral portion of the wire body 10 and the inner peripheral portion of the outer member 5 (second outer coil 52), and an inner member 4A is arranged in the gap 15. The inner member 4A is an inner coil 41 (third coil) formed by winding a wire (third wire) into a coil shape around a central axis of the wire body 10, and the wire body 10 is inserted into the inner side thereof. In this manner, the inner member 4A (inner coil) can collectively cover the joint portion 14, the second constant outer diameter portion 24 on the distal end side of the joint portion 14, and the first constant outer diameter portion 31 on the proximal end side. The inner diameter and the outer diameter of the inner member 4A are respectively constant along the longitudinal direction of the wire.

In addition, in the inner member 4A, the distal end portion 42 thereof is supported by and fixed to the wire body 10, and the fixing material 12 is responsible for the fixing. That is, the distal end portion 42 of the inner member 4A is supported by and fixed to the wire body 10 via the fixing material 12. A proximal end portion 45 of the inner member 4A is not fixed to the wire body 10. Furthermore, the outer diameter of the wire for the inner coil 41 of the inner member 4A is larger than that of a gap between the wire body 10 and the inner member 4A. This causes the inner member 4A to be in a state of being cantilevered, and thus, the proximal end side portion thereof (proximal end portion 45) can be stretched in the longitudinal direction of the wire. Portions other than the portion fixed by the fixing material 12 in the distal end portion 42 of the inner member 4A are arranged in a freely stretchable state along the longitudinal direction of the wire body 10.

According to this configuration, even when torque is applied to the guidewire 1 and a torsional load is also applied to the inner member 4A, the inner member 4A is stretchable in the longitudinal direction of the wire and thus, can escape the load. Accordingly, it is possible to deliberately prevent damage to the inner member 4A.

Note that, the fixing material 12 not only fixes the outer member 5 but also fixes the inner member 4A. Accordingly, it is possible to omit a manufacturing step of separately providing a member for fixing the inner member 4A, thereby enabling the structure of the guidewire 1 to be simplified.

When the guidewire 1 is used, torque acting around the axis thereof, a pushing force acting from the proximal end side, a pressing force acting from the curved blood vessel (force which bends the guidewire 1), and other forces are all applied to the guidewire 1. Therefore, a corresponding stress is generated in the joint portion 14. However, the stress is reliably relieved by the inner member 4A which is arranged as described above. This can reliably prevent a problem in which the guidewire 1 is unintentionally bent in the joint portion 14 or is broken in the joint portion 14 while the guidewire 1 is used (operated). Accordingly, the guidewire 1 has excellent operability, that is, excellent torque transmission performance, pushing performance, and kink resistance.

In addition, the inner member 4A allows smooth transition of the rigidity from the second wire 3 to the first wire 2. The vicinity of the proximal end portion of the first wire 2, whose rigidity is lower than that of the second wire 3, is likely to be largely deformed with respect to the bending stress. However, even when the vicinity of the proximal end portion of the first wire 2 which is covered with the inner member 4A is bent, the inner member 4A can prevent excessive curving-deformation. That is, an inner surface of the inner member 4A on the outer curving side comes into contact with an outer surface of the proximal end portion of the first wire 2, thereby suppressing the bending. The wires for the inner coil 41 of the inner member 4A on the inner curving side are gathered and come into contact with each other. Accordingly, it is possible to prevent excessive bending in the proximal end portion of the first wire 2. This enables the guidewire 1 to be smoothly curved even in the vicinity of the joint portion 14 when the guidewire 1 is inserted into the curved blood vessel, thereby improving the operability.

As illustrated in FIG. 1, in the inner member 4A, the inner diameter thereof is larger than the outer diameter of the joint portion 14, and the outer diameter is smaller than the inner diameter of the second outer coil 52 (outer member 5). This causes an inner peripheral portion 43 of the inner member 4A to be spaced apart from an outer peripheral portion 242 of the second constant outer diameter portion 24 of the first wire 2 and an outer peripheral portion 312 of the first constant outer diameter portion 31 of the second wire 3. In addition, an outer peripheral portion 44 of the inner member 4A is caused to be spaced apart from an inner peripheral portion 522 of the second outer coil 52. This separation and a synergistic effect of the stretchable inner member 4A can reliably prevent a case where one wire out of the adjacent wires for the inner coil 41 rides on the other wire, which can occur while the guidewire 1 is used, that is, positional deviation between the wires for the inner coil 41.

In addition, as illustrated in FIG. 1, a horizontal cross-sectional shape of the wire for the inner coil 41 is a circular shape. Then, it is preferable that the diameter of the wire for the inner coil 41 is the same as or smaller than the diameter of the second wire 521 forming the second outer coil 52. According to this configuration, it is possible to increase the diameter of the second wire 521 of the second outer coil 52 while maintaining a minimized gap between the second outer coil 52 and the inner member 4A. Therefore, it is possible to prevent a positional deviation between the second wires 521 of the second outer coil 52. Furthermore, the constituting material of the wire for the inner coil 41 (inner member 4A) is the same as the constituting material of the first wire 511 (first outer coil 51). For example, as described above, stainless steel can be used.

In addition, it is preferable to densely wind the wires for the inner coil 41 of the inner member 4A. This allows the inner member 4A to be provided with initial tension. Power then generated by the inner member 4A (i.e., when attempting to unwind) demonstrates an effect of preventing the wire body 10 from being curved.

Furthermore, the diameter of the wire for the inner coil 41 of the inner member 4A is larger than the diameter of the gap between the inner member 4A and the second outer coil 52. Therefore, it is possible to prevent the positional deviation between the wires for the inner coil 41. In addition, the diameter of the second wire 521 of the second outer coil 52 is larger than the diameter of the gap between the inner member 4A and the second outer coil 52. Therefore, it is possible to prevent a positional deviation between the second wires 521.

The inner member 4A configured with such a wire for the inner coil 41 has moderate flexibility and straightness. This can more reliably relieve the stress generated in the joint portion 14 and reliably prevent the inner member 4A itself from excessively interfering with the curving when the guidewire 1 is curved.

In addition, a winding direction of the wire for the inner coil 41 is the same as respective winding directions of the first wire 511 and the second wire 521. In this manner, diameter decreasing and diameter increasing are the same as each other in each coil (first outer coil 51 and second outer coil 52) with respect to the rotation direction around the axis of the guidewire 1. Accordingly, there is an advantage in that it is possible to prevent damage to each coil.

Figure 2:
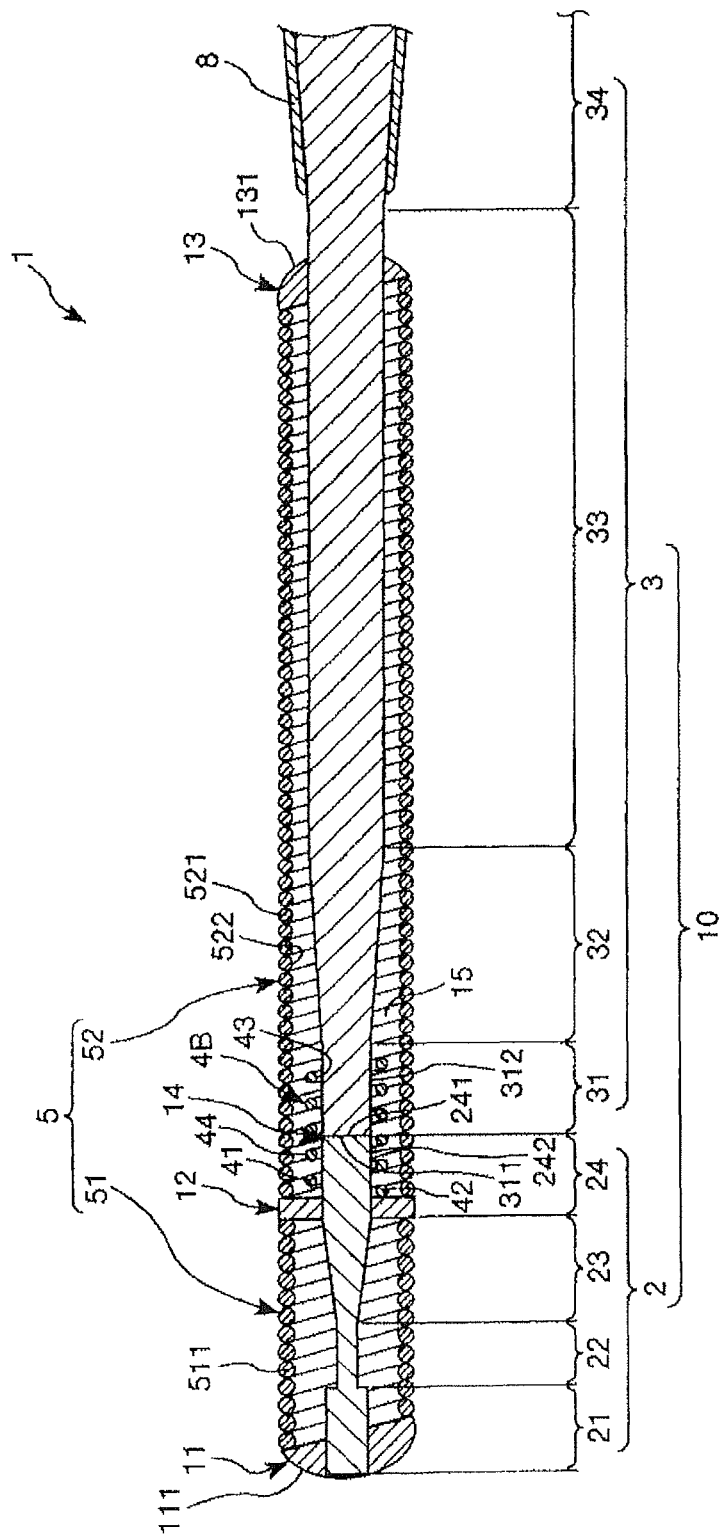
FIG. 2 is a longitudinal cross-sectional view illustrating a second exemplary embodiment of a guidewire according to the disclosure.

FIG. 2 is a longitudinal cross-sectional view illustrating a second exemplary embodiment of a guidewire according to the disclosure herein.

Hereinafter, the second exemplary embodiment of the guidewire according to the disclosure will be described with reference to the drawing. However, points different from those in the above-described embodiment will be mainly described, and description of the same points will be omitted.

The second exemplary embodiment is the same as the first embodiment except that a shape of an inner member is different.

As illustrated in FIG. 2, in the guidewire 1 of the second exemplary embodiment, an inner member 4B is configured so that the adjacent wires for the inner coil 41 are spaced apart from each other in a natural state, and the inner member 4B is coarsely wound. This causes the inner member 4B to have initial tension which is weaker than that of the densely wound second outer coil 52.

This coarsely wound inner member 4B becomes more likely to be stretched in the longitudinal direction of the wire. This can more reliably prevent a case where one wire out of the adjacent wires for the inner coil 41 rides on the other wire, which can occur while the guidewire 1 is used. In addition, there is also an advantage in that it is possible to prevent the operability from being degraded, since the provided flexibility allows a smooth change in physical properties.

Figure 3:
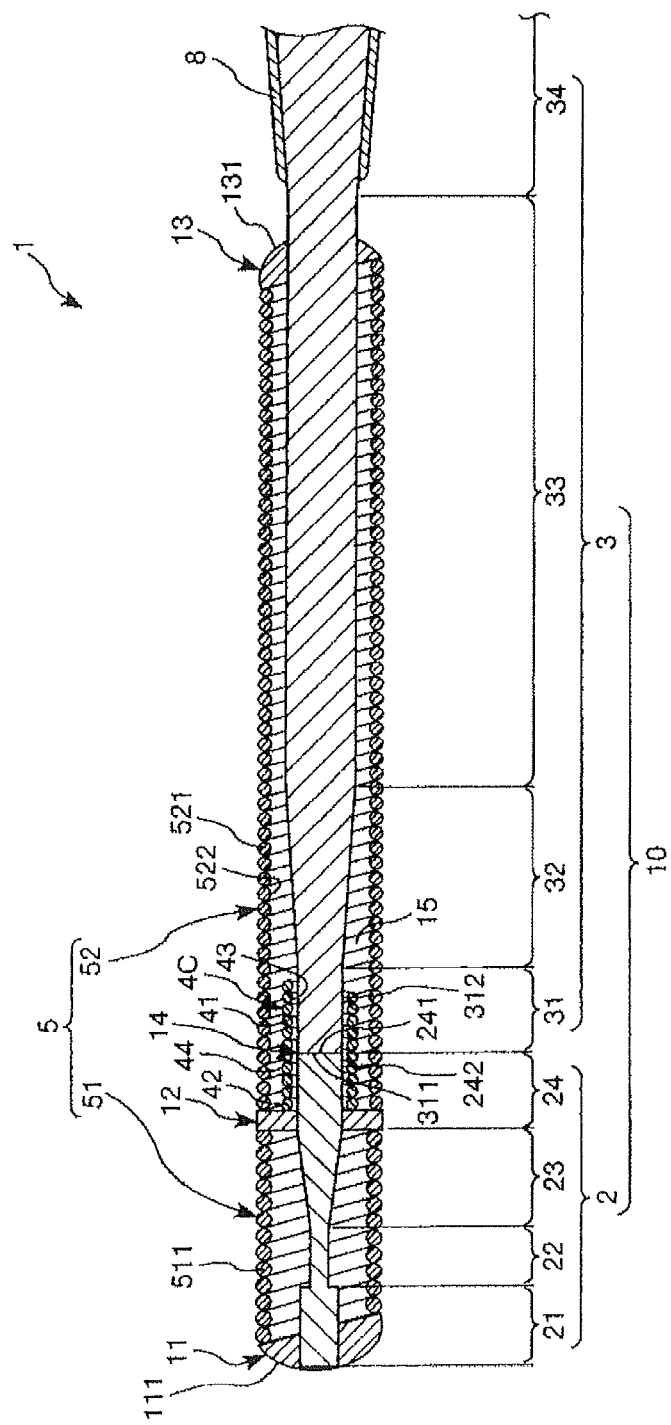
FIG. 3 is a longitudinal cross-sectional view illustrating a third exemplary embodiment of a guidewire according to the disclosure.

FIG. 3 is a longitudinal cross-sectional view illustrating a third exemplary embodiment of a guidewire according to the disclosure herein.

Hereinafter, the third embodiment of the guidewire according to the disclosure will be described with reference to the drawing. However, points different from those in the above-described embodiments will be mainly described, and description of the same points will be omitted.

The third exemplary embodiment is the same as the first embodiment except that a shape of an inner member is different.

As illustrated in FIG. 3, in the guidewire 1 of the third embodiment, the winding direction of the wire for the inner coil 41 forming an inner member 4C is opposite to the winding direction of a wire for the second outer member 521 forming the second outer coil 52 (the same winding direction is applied to a wire for the first outer member 511). This reliably prevents the guidewire 1 from being unintentionally deformed since the wire for the inner coil 41 is caught in a portion between the adjacent wires for the second outer member 521 while the guidewire 1 is used.

Figure 4:
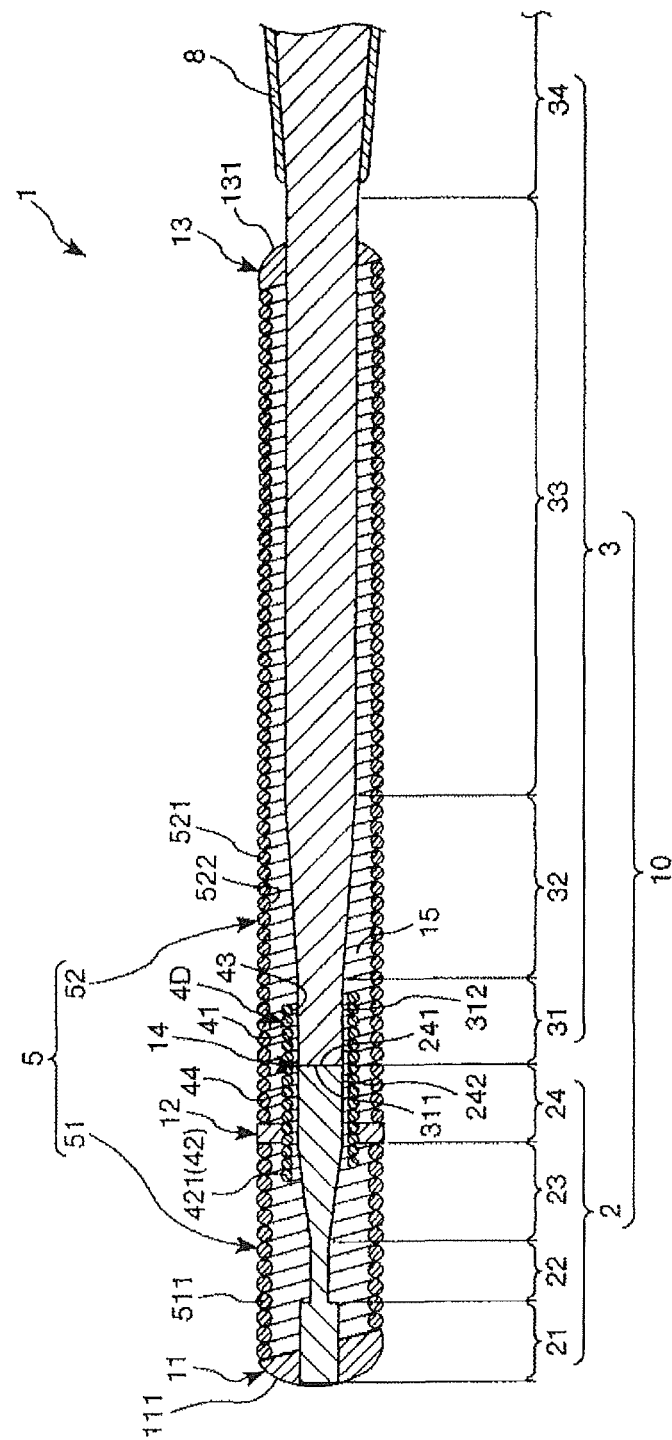
FIG. 4 is a longitudinal cross-sectional view illustrating a fourth exemplary embodiment of a guidewire according to the disclosure.

FIG. 4 is a longitudinal cross-sectional view illustrating a fourth exemplary embodiment of a guidewire according to the disclosure herein.

Hereinafter, the fourth exemplary embodiment of the guidewire according to the disclosure will be described with reference to the drawing. However, points different from those in the above-described embodiments will be mainly described, and description of the same points will be omitted.

The fourth exemplary embodiment is the same as the first embodiment except that a length of an inner member is different.

As illustrated in FIG. 4, in the guidewire 1 of the fourth embodiment, an inner member 4D has a protruding portion 421 which is formed by the distal end portion 42 of the inner member 4D inserted into the fixing material 12 to protrude and extend from the fixing material 12 in a direction toward the distal end. A protruding amount of the protruding portion 421 is not particularly limited, but for example, it is preferable that the protruding amount is 1% to 34% of the overall length of the inner member 4D.

The protruding portion 421 functions so as to fill a portion between the first outer coil 51 and the first wire 2. This can more reliably prevent a case where one wire out of the adjacent first wires 511 rides on the other wire, in the proximal end portion of the first outer coil 51, which can occur while the guidewire 1 is used. Note that, this riding is more likely to occur in the proximal end portion as compared to the distal end portion of the coil.

Figure 5:
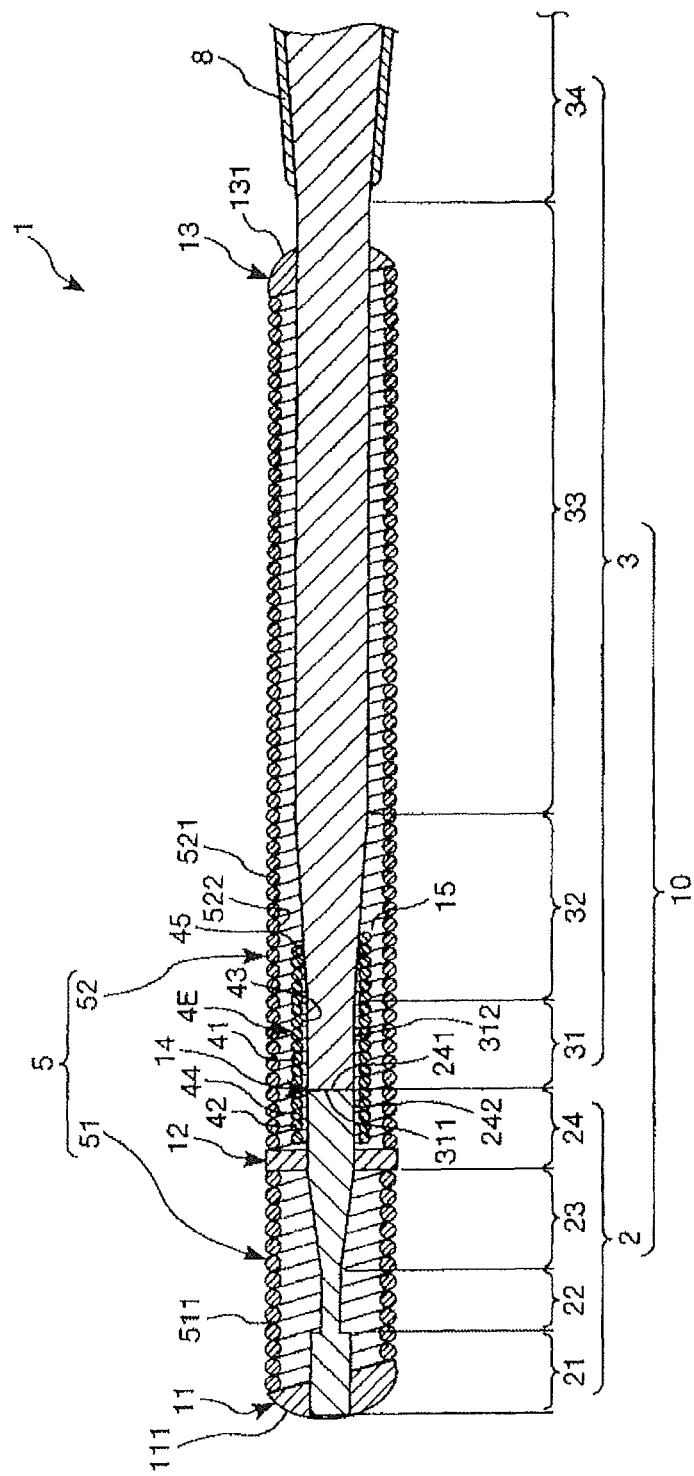
FIG. 5 is a longitudinal cross-sectional view illustrating a fifth exemplary embodiment of a guidewire according to the disclosure.

FIG. 5 is a longitudinal cross-sectional view illustrating a fifth exemplary embodiment of a guidewire according to the disclosure herein.

Hereinafter, the fifth exemplary embodiment of the guidewire according to the disclosure will be described with reference to the drawing. However, points different from those in the above-described embodiments will be mainly described, and description of the same points will be omitted.

The fifth exemplary embodiment is the same as the first embodiment except that a support location of the inner member with respect to the wire body is different.

As illustrated in FIG. 5, in the guidewire 1 of the fifth embodiment, an inner member 4E is arranged in a stretchable state from the distal end portion 42 thereof to the proximal end portion 45. More specifically, in the inner member 4E, the distal end portion 42 thereof is spaced apart from the fixing material 12, and the proximal end portion 45 is located in the tapered portion 32 of the second wire 3. It is preferable that the distal end portion 42 of the inner member 4E leave a gap from the fixing material 12, whose size is equal to or smaller than that of a diameter of the wire for the inner coil 41. This can prevent damage to the inner member 4E which may occur due to excessive loosening of the wire body 10 in an axial direction. In addition, in the proximal end portion 45 of the inner member 4E, the outer surface of the first tapered portion 32 and the inner surface of the proximal end portion 45 are in a contact state, in a location where the inner diameter of the inner member 4E reaches the outer diameter of the first tapered portion 32 of the second wire 3. In this state, a movement of the inner member 4E to the proximal end side of the wire body 10 is substantially restricted. In this manner, the inner member 4E is in a state having no fixed point with respect to the wire body 10, and thus, the entire body can be stretched in the longitudinal direction of the wire. According to this configuration, even when the torque is applied to the guidewire 1 and a shaking load is also applied to the inner member 4E, the inner member 4E is stretchable in the longitudinal direction of the wire and thus, can escape the load. Accordingly, it is possible to deliberately prevent damage to the inner member 4E. In addition, this can more reliably prevent a case where one wire out of the adjacent wires for the inner coil 41 of the inner member 4E rides on the other wire, which can occur while the guidewire 1 is used.

Figure 6:
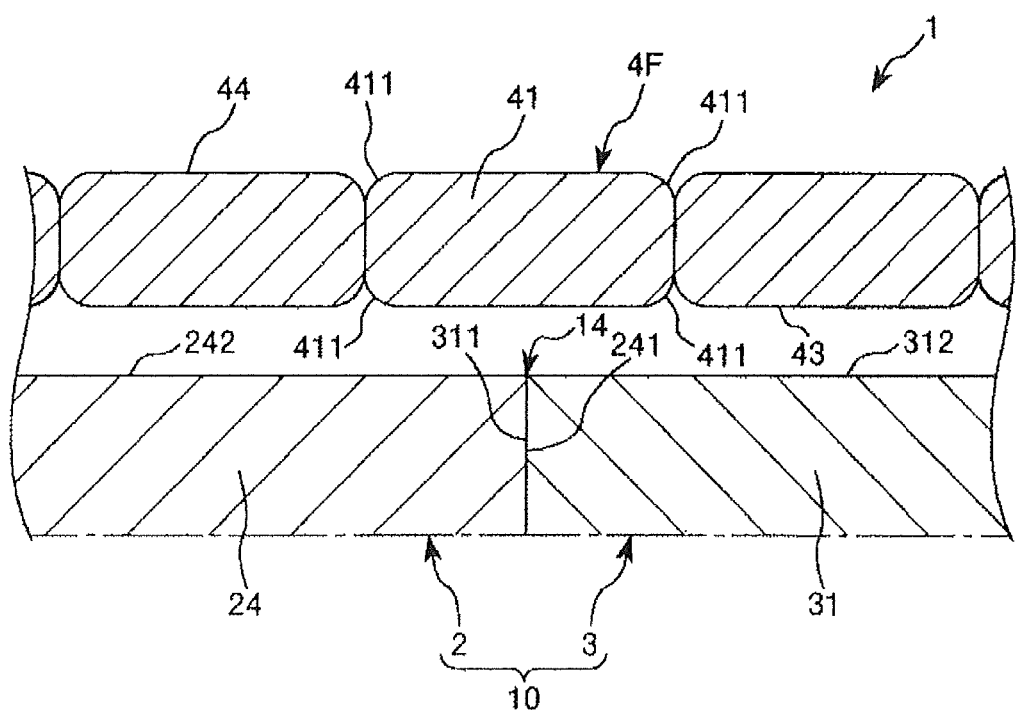
FIG. 6 is an enlarged longitudinal cross-sectional view of an inner member included in a guidewire (sixth exemplary embodiment) according to the disclosure.

FIG. 6 is an enlarged longitudinal cross-sectional view of an inner member included in a guidewire (sixth exemplary embodiment) according to the disclosure herein.

Hereinafter, the sixth exemplary embodiment of the guidewire according to the disclosure will be described with reference to the drawing. However, points different from those in the above-described embodiments will be mainly described, and description of the same points will be omitted.

The sixth embodiment is the same as the first embodiment except that a horizontal cross-sectional shape of a wire for the inner member is different.

As illustrated in FIG. 6, in the guidewire 1 of the sixth embodiment, the horizontal cross-sectional shape of the wire for the inner coil 41 which configures an inner member 4F is a flat shape. In the illustrated configuration, the shape is a rectangular shape, and the longitudinal direction thereof is the same as the longitudinal direction of the wire. In addition, the rectangular shape may be configured so that each corner portion 411 has a right angle, respectively. However, it is preferable that the corner portion be rounded as illustrated in FIG. 6.

Since the horizontal cross-sectional shape of the wire for the inner coil 41 has a rectangular shape, the vicinity of the proximal end portion of the first wire 2 whose rigidity is lower than that of the second wire 3 is likely to be largely deformed with respect to the bending stress. However, by covering the vicinity of the proximal end portion with the inner member 4F, it is possible to further suppress excessive curving-deformation in the vicinity of the proximal end portion of the first wire 2 whose rigidity is lower than that of the second wire 3. In addition, the inner member 4F is relatively thin, and accordingly, contributes to a decrease in the diameter of the guidewire 1. The thickness of the wire for the inner coil 41 depends on the diameter of the wire of the outer coil 52. For example, when the diameter of the wire of the outer coil 52 is 40 μm to 50 μm, the thickness is preferably 10 μm to 40 μm, and is more preferably 20 μm to 30 μm.

Figure 7:
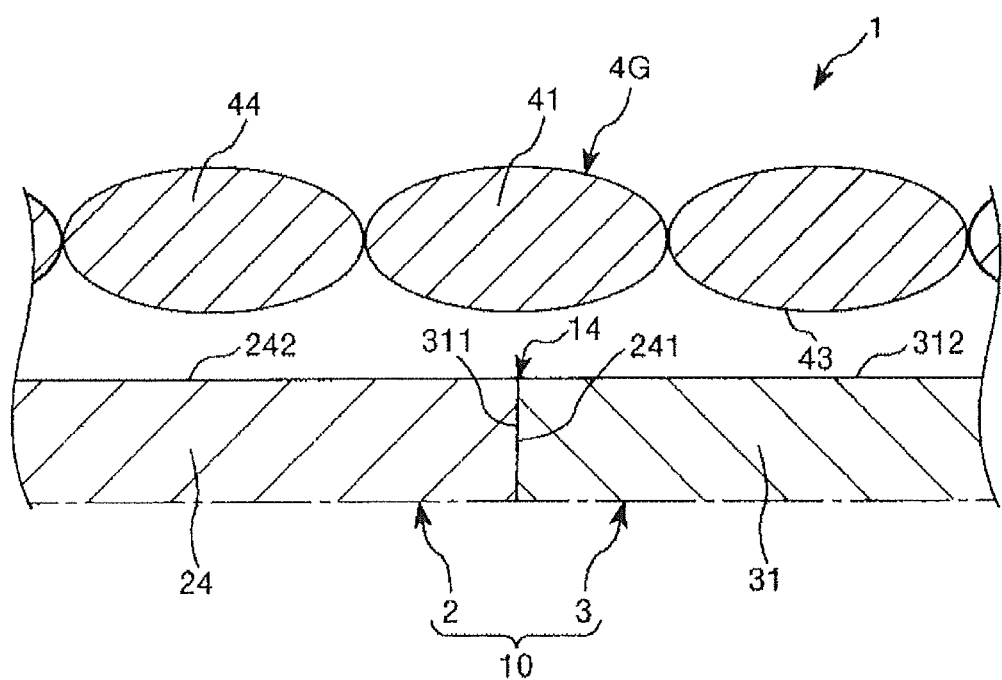
FIG. 7 is an enlarged longitudinal cross-sectional view of an inner member included in a guidewire (seventh exemplary embodiment) according to the disclosure.

FIG. 7 is an enlarged longitudinal cross-sectional view of an inner member included in a guidewire (seventh exemplary embodiment) according to the disclosure herein.

Hereinafter, the seventh exemplary embodiment of the guidewire according to the disclosure will be described with reference to the drawing. However, points different from those in the above-described embodiments will be mainly described, and description of the same points will be omitted.

The seventh embodiment is the same as the first embodiment except that a horizontal cross-sectional shape of a wire for the inner member is different.

As illustrated in FIG. 7, in the guidewire 1 of the seventh embodiment, the horizontal cross-sectional shape of the wire for the inner coil 41 which forms an inner member 4G is a flat shape. In the illustrated configuration, the shape is an elliptical shape, and the longitudinal direction thereof is the same as the longitudinal direction of the wire.

Since the horizontal cross-sectional shape of the wire for the inner coil 41 is the elliptical shape, the vicinity of the proximal end portion of the first wire 2 whose rigidity is lower than that of the second wire 3 is likely to be largely deformed with respect to the bending stress. However, by covering the vicinity of the proximal end portion with the inner member 4G, it is possible to further suppress excessive curving-deformation in the vicinity of the proximal end portion of the first wire 2 whose rigidity is lower than that of the second wire 3. In addition, the inner member 4G is relatively thin, and accordingly, contributes to a decrease in the diameter of the guidewire 1.

Figure 8:
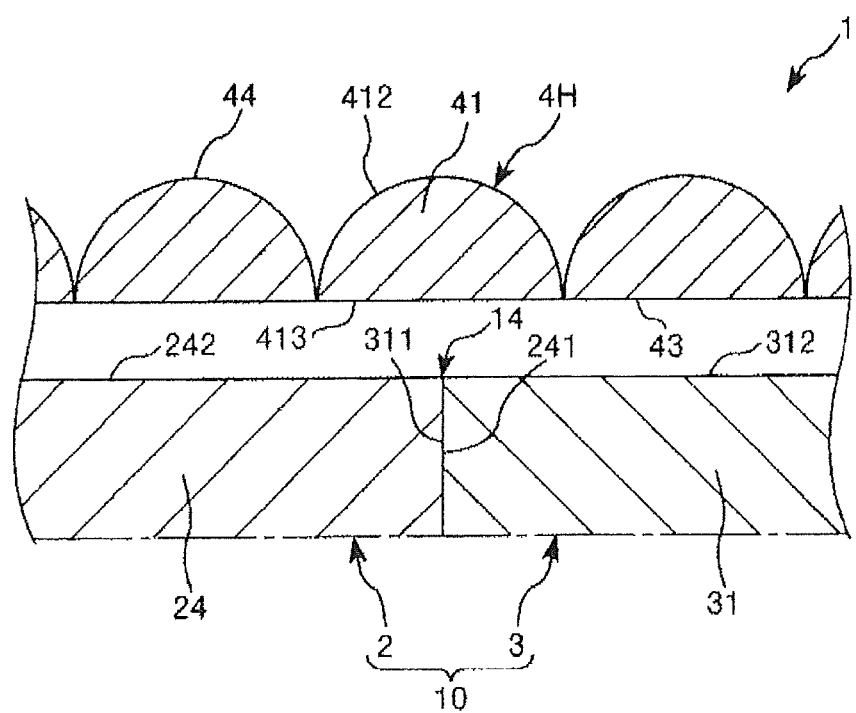
FIG. 8 is an enlarged longitudinal cross-sectional view of an inner member included in a guidewire (eighth exemplary embodiment) according to the disclosure.

FIG. 8 is an enlarged longitudinal cross-sectional view of an inner member included in a guidewire (eighth exemplary embodiment) according to the disclosure herein.

Hereinafter, the eighth embodiment of the guidewire according to the disclosure will be described with reference to the drawing. However, points different from those in the above-described embodiments will be mainly described, and description of the same points will be omitted.

The eighth embodiment is the same as the first embodiment except that a horizontal cross-sectional shape of a wire for the inner member is different.

As illustrated in FIG. 8, in the guidewire 1 of the eighth embodiment, the horizontal cross-sectional shape of the wire for the inner coil 41 which forms an inner member 4H is a flat shape. In the illustrated configuration, the shape is a semicircular shape, and the longitudinal direction thereof is the same as the longitudinal direction of the wire.

Since the horizontal cross-sectional shape of the wire for the inner coil 41 is the semicircular shape, the vicinity of the proximal end portion of the first wire 2 whose rigidity is lower than that of the second wire 3 is likely to be largely deformed with respect to the bending stress. However, by covering the vicinity of the proximal end portion with the inner member 4H, it is possible to further suppress excessive curving-deformation in the vicinity of the proximal end portion of the first wire 2 whose rigidity is lower than that of the second wire 3. In addition, the inner member 4H is relatively thin, and accordingly, contributes to a decrease in the diameter of the guidewire 1.

In addition, in the wire for the inner coil 41, a plane 413 opposite to a curved surface 412 thereof faces the wire body 10. This allows the inner member 4H to be stably placed on the wire body 10.

The inner members 4F to 4H of the sixth to eighth exemplary embodiments have an aspect in which the adjacent wires for the inner coil 41 are in contact with each other. However, the adjacent wires for the inner coil 41 may have a gap therebetween.

Figure 9:
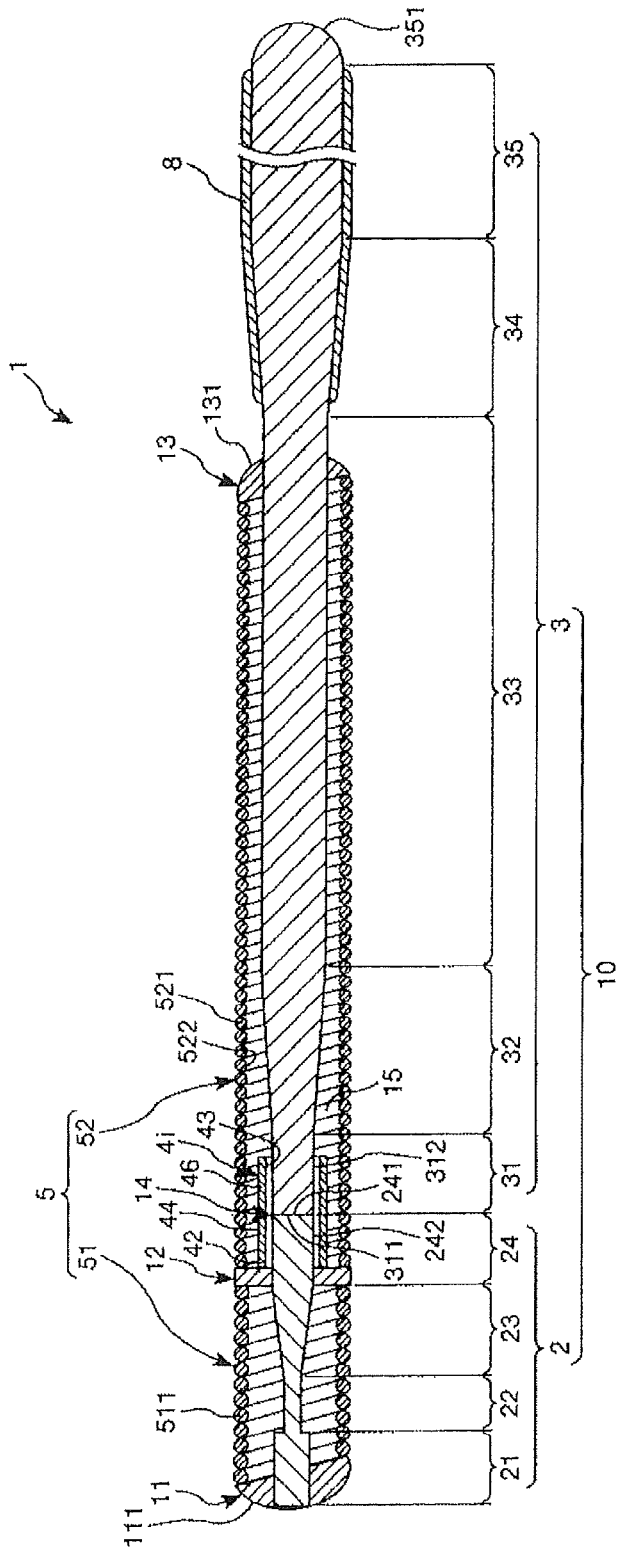
FIG. 9 is a longitudinal cross-sectional view illustrating a ninth exemplary embodiment of a guidewire according to the disclosure.

FIG. 9 is a longitudinal cross-sectional view illustrating a ninth exemplary embodiment of a guidewire according to the disclosure herein, and is a side view of an inner member included in the guidewire illustrated in FIG. 9.

Hereinafter, the ninth embodiment of the guidewire according to the disclosure will be described with reference to the drawing. However, points different from those in the above-described embodiments will be mainly described, and description of the same points will be omitted.

The ninth embodiment is the same as the first embodiment except that a shape of the inner member is different.

Figure 10:
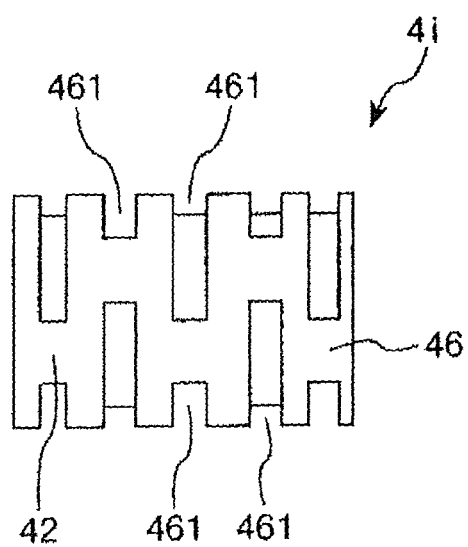
FIG. 10 is a side view of an inner member included in the guidewire illustrated in FIG. 9.

As illustrated in FIGS. 9 and 10, in the guidewire 1 of the ninth embodiment, an inner member 4I is formed by a pipe (tube). The inner member 4I (pipe) has multiple penetrating portions 461 which penetrate a tube wall 46 (refer to FIG. 10). The penetrating portions 461 are formed as multiple slots along a circumferential direction of the inner member 4I. Positions of the adjacent slots are different from one another.

This inner element 4I has the sufficient flexibility, and thus, it is possible to relieve the stress in the joint portion 14. Accordingly, as described above, the operability is improved in the guidewire 1.

Note that, each of the penetrating portions 461 has a slot shape in the configuration illustrated in FIG. 10. However, without being limited thereto, for example, the shape may be a circular shape, a spiral shape, an elongated notch (slit) shape, or a strip-like notch shape.

The configuration of the inner member 4I illustrated in FIG. 10 can also be used as the outer member 5 in the above-described embodiments.

Hitherto, the guidewire of the disclosure herein has been described with reference to the illustrated exemplary embodiments. However, the present invention is not limited thereto. The portions constituting the guidewire each can be substituted by any desired configuration which can demonstrate the same function. In addition, any desired constituting element may be added thereto.

In addition, the guidewire of the present invention may be formed by combining any two or more desired configurations (features) within the above-described exemplary embodiments.

In addition, the inner peripheral portion of the inner member is spaced apart from the outer peripheral portion of the wire body in the embodiments. However, without being limited thereto, the inner peripheral portion of the inner member may be in contact with the outer peripheral portion of the wire body.

In addition, the inner member is cantilevered in the above-described embodiments. However, without being limited thereto, the inner member may be supported in both ends. For example, when the inner member is supported in both ends, the torque transmission performance of the guide wire is improved.

In addition, a resin layer may be interposed between the outer member and the inner member.

A guidewire of the disclosure herein includes a wire body that has a first wire which is arranged on a distal end side and a second wire which is arranged on a proximal end side of the first wire and is formed of a material whose rigidity is higher than that of a constituting material of the first wire, and in which a proximal end surface of the first wire and a distal end surface of the second wire are joined to each other so as to form a joint portion, an outer member that is arranged on an outer peripheral side of the wire body, that forms a tubular shape which covers the wire body at least from a distal end portion of the first wire to the joint portion, and that has flexibility, and an inner member that is arranged between an outer peripheral portion of the wire body and an inner peripheral portion of the outer member, and that covers the joint portion. The inner member is an inner coil formed by winding a wire for the inner member into a coil shape.

Therefore, when the guidewire is used, a torque acting around an axis thereof, a pushing force acting from a proximal end side thereof, and a pressing force acting from a curved blood vessel (force which bends the guidewire) are all applied to the guidewire. In this case, stress is generated in a joined portion formed by a first wire and a second wire being joined to each other. However, according to the disclosure here, the stress is reliably relieved by the inner member. This can reliably prevent a problem in which the guidewire is unintentionally bent in the joint portion or is broken in the joint portion, while the guidewire is used (operated). Accordingly, the guidewire is excellent in operability such as torque transmission performance, pushing performance, and kink resistance, for example. Therefore, the guidewire disclosed here has industrial applicability.

The detailed description above describes a guide wire disclosed by way of example. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A guidewire comprising:
   a wire body that has a first wire arranged on a distal end side and a second wire arranged on a proximal end side of the first wire, the second wire being formed of a material whose rigidity is higher than that of a material forming the first wire, and a proximal-most end surface of the first wire and a distal-most end surface of the second wire being joined to each other so as to form a joint portion;
   an outer member arranged on an outer peripheral side of the wire body and forming a tubular shape which covers the wire body at least from a distal end portion of the first wire to the joint portion, the outer member having flexibility; and
   an inner member having a distal end and a proximal end, the inner member being arranged between an outer peripheral portion of the wire body and an inner peripheral portion of the outer member, and covering the joint portion;
   wherein the inner member is an inner coil formed by winding a wire for the inner member into a coil shape; and
   wherein a distal end of the inner member is not fixed to the wire body.

2. The guidewire according to claim 1, wherein the inner coil has a distal end portion and a proximal end portion, and at least any one of the distal end portion and the proximal end portion is stretchable.

3. The guidewire according to claim 1, wherein the joint portion has an outer diameter which is the same as an outer diameter of a proximal end of the first wire on a distal end side and an outer diameter of a distal end of the second wire on a proximal end side, respectively, and
   wherein an inner diameter of the inner coil is larger than an outer diameter of the joint portion.

4. The guidewire according to claim 1, wherein a horizontal cross-sectional shape of the wire for the inner member has a circular shape or a flat shape.

5. The guidewire according to claim 4, wherein the wire for the inner member has a rectangular shape.

6. The guidewire according to claim 4, wherein the wire for the inner member has an elliptical shape.

7. The guidewire according to claim 4, wherein the wire for the inner member has a semicircular shape.

8. The guidewire according to claim 1, wherein the outer member is configured to have a first outer coil located on a distal end side and formed by winding a wire for a first outer member into a coil shape and a second outer coil connected to a proximal end side of the first outer coil and formed by winding a wire for a second outer member into a coil shape; and wherein the wire for the inner member is thinnest wire among the wire for the first outer member, the wire for the second outer member, and the wire for the inner member.

9. The guidewire according to claim 8, wherein a winding direction of the wire forming the inner coil is the same as a winding direction of a wire forming the first outer coil and the second outer coil.

10. The guidewire according to claim 8, wherein a winding direction of the wire forming the inner coil is opposite to a winding direction of the wire forming the second outer coil.

11. The guidewire according to claim 1, wherein the inner member relieves stress generated in the joint portion when the guidewire is used.

12. The guidewire according to claim 1, wherein the inner coil forming the inner member is coarsely wound such that adjacent windings of the inner coil are spaced apart.

13. The guidewire according to claim 1, wherein the outer member is fixed to the wire body via a fixing material disposed at a location where the inner member is arranged between the wire body and the outer member.

14. The guidewire according to claim 13, wherein the inner member protrudes distally from the fixing material.

15. The guidewire according to claim 13, wherein the distal end of the inner member is spaced proximally from the fixing material.

16. The guidewire according to claim 15, wherein the proximal end of the inner member contacts the second wire.

17. The guidewire according to claim 1, wherein the inner member includes only one fixing portion.

18. The guidewire according to claim 17, wherein the fixing portion of the inner member is disposed distally relative to the joint portion of the wire body.

19. The guidewire according to claim 14, wherein a protruding amount of the protruding portion from the fixing material is 1% to 34% of an overall length of the inner member.

* * * * *